United States Patent
Hamachi

(10) Patent No.: US 7,521,250 B2
(45) Date of Patent: Apr. 21, 2009

(54) FLUORESCENT SENSOR FOR PHOSPHATE ION AND PHOSPHORYLATED PEPTIDE

(75) Inventor: Itaru Hamachi, Fukuoka (JP)

(73) Assignee: Japan Science and Technology Agency, Saitama (JP)

( * ) Notice: Subject to any disclaimer, the term of this patent is extended or adjusted under 35 U.S.C. 154(b) by 827 days.

(21) Appl. No.: 10/505,056

(22) PCT Filed: Jan. 27, 2003

(86) PCT No.: PCT/JP03/00705

§ 371 (c)(1),
(2), (4) Date: Aug. 19, 2004

(87) PCT Pub. No.: WO03/071280

PCT Pub. Date: Aug. 28, 2003

(65) Prior Publication Data

US 2005/0148086 A1    Jul. 7, 2005

(30) Foreign Application Priority Data

Feb. 22, 2002    (JP)    ................. 2002-045846

(51) Int. Cl.
*G01N 33/00*    (2006.01)
(52) U.S. Cl. ..................... 436/86; 436/87; 436/172; 435/40.5
(58) Field of Classification Search ............... 436/546, 436/101, 110, 125, 126, 140; 422/15, 37, 422/82.07, 82.08
See application file for complete search history.

(56) References Cited

FOREIGN PATENT DOCUMENTS

JP    01-253871    *    9/2001

OTHER PUBLICATIONS

First Artificial Receptors and Chemosensors toward Phosphorylated Peptide in Aqueous Solution. Akio Ojida, Yasuko Mito-oka, Masa-aki Inoue, and Itaru Hamachi. Journal of American Chemical Society 2002, 124(22), 6256-6258.*

Yasuko Mito-oka, Shinya Tsukiji, Takashi Hiraoka, Noriyuki Kasagi, Seiji Khinkai, and Itaru Hamachi Zn(II)dipicolylamine-based artifucial receptor as a new entry for surface recognition of alpha helical peptides in aqueous solution. Tetrahedron Letters 42 (2001) 7059-7062.*

* cited by examiner

*Primary Examiner*—Jill Warden
*Assistant Examiner*—Dwan A Gerido
(74) *Attorney, Agent, or Firm*—Fay Sharpe LLP

(57) ABSTRACT

Disclosed is a fluorescent sensor for phosphate ion and phosphorylated peptide, which comprises a phosphate anion-selective fluorescent compound expressed by the following general formula (1). In the formula (1), FL represents a fluorescent functional group or atomic group having an aromatic ring or heterocyclic ring (for example, dimethylanthlyl group), and X represents a functional group or atomic group which will be liberated in an aqueous solution to form an anion (for example, $NO_3$):

$$X\text{---}Zn\text{---}N\text{---}FL\text{---}N\text{---}Zn\text{---}X \quad (1)$$

10 Claims, 2 Drawing Sheets

| peptide 1 | AcNH-Glu-Glu-Glu-Ile-pTyr-Glu-Glu-Phe-Asp-CONH$_2$ (v-Src) |
| peptide 1' | AcNH-Glu-Glu-Glu-Ile-Tyr-Glu-Glu-Phe-Asp-CONH$_2$ |
| peptide 2 | AcNH-Arg-Arg-Phe-Gly-pSer-Ile-Arg-Arg-Phe-CONH$_2$ (Bck2) |
| peptide 3 | AcNH-Lys-Ser-Gly-pTyr-Leu-Ser-Ser-Glu-CONH$_2$ (EGFR) |

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial
<220> FEATURE:
<223> OTHER INFORMATION: Synthesized with peptide synthesizer using HBTU
      as condensation agent
<220> FEATURE:
<221> NAME/KEY: MOD_RES
<222> LOCATION: (1)..(1)
<223> OTHER INFORMATION: acetylation
<220> FEATURE:
<221> NAME/KEY: MOD_RES
<222> LOCATION: (5)..(5)
<223> OTHER INFORMATION: phosphorylation
<220> FEATURE:
<221> NAME/KEY: MOD_RES
<222> LOCATION: (9)..(9)
<223> OTHER INFORMATION: amidation

<400> SEQUENCE: 1

Glu Glu Glu Ile Tyr Glu Glu Phe Asp
1               5

<210> SEQ ID NO 2
<211> LENGTH: 9
<212> TYPE: PRT
<213> ORGANISM: Artificial
<220> FEATURE:
<223> OTHER INFORMATION: Synthesized with peptide synthesizer using HBTU
      as condensation agent
<220> FEATURE:
<221> NAME/KEY: MOD_RES
<222> LOCATION: (1)..(1)
<223> OTHER INFORMATION: acetylation
<220> FEATURE:
<221> NAME/KEY: MOD_RES
<222> LOCATION: (9)..(9)
<223> OTHER INFORMATION: amidation
```

<400> SEQUENCE: 2

Glu Glu Glu Ile Tyr Glu Glu Phe Asp
1               5

<210> SEQ ID NO 3
<211> LENGTH: 9
<212> TYPE: PRT
<213> ORGANISM: Artificial
<220> FEATURE:
<223> OTHER INFORMATION: Synthesized with peptide synthesizer using HBTU
      as condensation agent
<220> FEATURE:
<221> NAME/KEY: MOD_RES
<222> LOCATION: (1)..(1)
<223> OTHER INFORMATION: acetylation
<220> FEATURE:
<221> NAME/KEY: MOD_RES
<222> LOCATION: (5)..(5)
<223> OTHER INFORMATION: phosphorylation
<220> FEATURE:
<221> NAME/KEY: MOD_RES
<222> LOCATION: (9)..(9)
<223> OTHER INFORMATION: amidation

<400> SEQUENCE: 3

Arg Arg Phe Gly Ser Ile Arg Arg Phe
1               5

<210> SEQ ID NO 4
<211> LENGTH: 8
<212> TYPE: PRT
<213> ORGANISM: Artificial
<220> FEATURE:
<223> OTHER INFORMATION: Synthesized with peptide synthesizer using HBTU
      as condensation agent
<220> FEATURE:
<221> NAME/KEY: MOD_RES
<222> LOCATION: (1)..(1)
<223> OTHER INFORMATION: acetylation
<220> FEATURE:
<221> NAME/KEY: MOD_RES
<222> LOCATION: (4)..(4)
<223> OTHER INFORMATION: phosphorylation
<220> FEATURE:
<221> NAME/KEY: MOD_RES
<222> LOCATION: (8)..(8)
<223> OTHER INFORMATION: amidation

<400> SEQUENCE: 4

Lys Ser Gly Tyr Leu Ser Ser Glu
1               5

FLUORESCENT SENSOR FOR PHOSPHATE ION AND PHOSPHORYLATED PEPTIDE

TECHNICAL FIELD

The present invention belongs to the technical field of anion detection, and particularly relates to a fluorescent sensor comprising a phosphate ion-selective fluorescent compound which exhibits a fluorescence change in the presence of phosphate anions in an aqueous solution corresponding to an in vivo environment and thus is suitable for use in the analysis of phosphate ions and phosphorylated peptides.

BACKGROUND ART

The phosphate anion plays an important role in vivo. For example, in the signal transmission system, a variety of information transmissions can be controlled via the phosphate functional groups of phosphorylated proteins or phospholipids. It is therefore expected that an established sensing system for detecting phosphate anions in an aqueous solution corresponding to an in vivo environment will serve as a basic tool in cell biology and other fields for the analysis of a number of in vivo processes, the results thereof contributing to the development of new medicines and reagents. For example, the recognition of an intracellular phosphorylation signal, a key reaction for the malignant alteration caused by an abnormal information transmission, will be effective in designing inhibitors and the like against such reaction.

A potential useful means for detecting anions such as phosphate anion will be a fluorescent probe composed of a compound which exhibits fluorescence change upon being combined specifically with the anions. A number of probes have hitherto been developed for detecting cations typified by metal ions. However, with regard to fluorescent probes for detecting anions, only a small number of probes have been proposed which function in organic solvents, and there is found almost nothing for use in a neutral aqueous solution such as an in vivo media. This is because anions are generally larger in size than metal ions and are therefore more influenced by hydration, resulting in difficulty in chelation. In addition, while it is possible, with a probe for detecting metal ions, to develop fluorescence change via coordination of functional groups present in the structure of the fluorescent compound, such as aromatic amino groups, with metal ions, similar phenomena are unlikely to be utilizable in the detection of anions. For these reasons, very few examples are found of fluorescent probes for detecting anions such as phosphate anions.

One rare example of a fluorescent probe for recognizing phosphate anion in an aqueous solution is the ruthenium-bipyridylpolyaza compound reported by Beer et al. (P. D. Beer et al., Angew. Chem. Int. Ed., 40, 486 (2001); P. D. Beer et al., J. Am. Chem. Soc., 119, 11864 (1997)). However, this compound exhibits a very low fluorescence change. Another rare example is found in the utilization of a boronic acid-diester compound as a fluorescent probe for detecting anions such as phosphate ion (Japanese Patent Application Publication 2001-133407).

The object of the present invention is to provide a novel sensor composed of a fluorescent probe which is capable of detecting phosphate ion with a high sensitivity.

DISCLOSURE OF THE INVENTION

Through extensive studies, the present inventors found that a zinc-dipicolylamine binuclear complex having a fluorescent functional group in the center is capable of selectively capturing phosphate anion in an aqueous solution corresponding to the physiological condition, producing a fluorescence change for the detection of the anion.

Thus, the above-mentioned object has been accomplished by providing a fluorescent sensor for phosphate ion and phosphorylated peptide, which comprises a phosphate anion-selective fluorescent compound expressed by the following general formula (1).

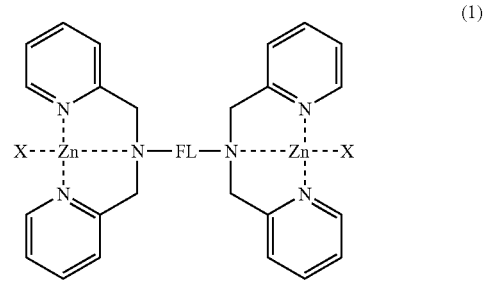

(1)

In the formula (1), FL represents a fluorescent functional group or atomic group having an aromatic ring or heterocyclic ring, and X represents a functional group or atomic group which will be liberated in an aqueous solution to form an anion.

BEST MODE FOR CARRYING OUT THE INVENTION

Figure 1:
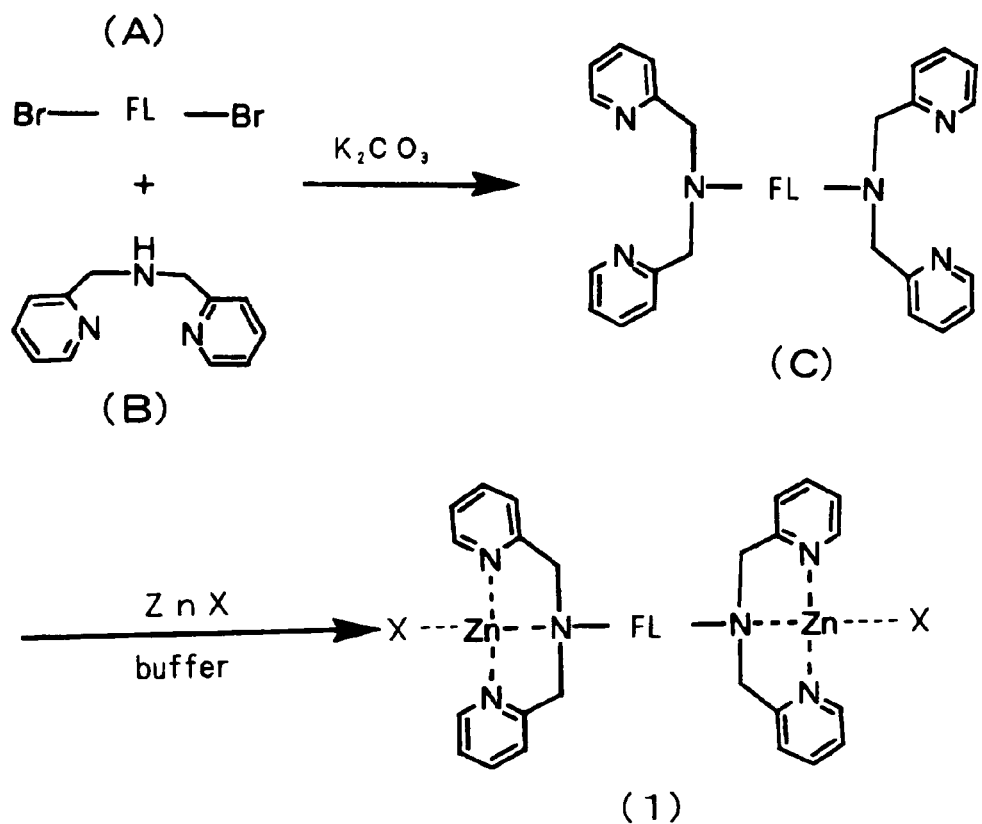
FIG. 1 outlines a scheme for synthesis of zinc-dipicolylamine binuclear complex for use in the fluorescent sensor of the present invention.
Figure 2:
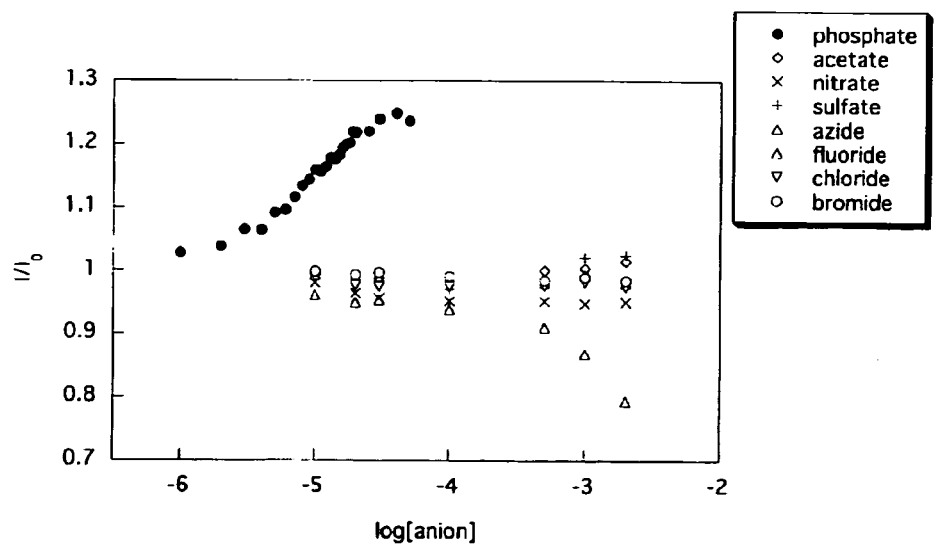
FIG. 2 illustrates an example of the measurements of the change in fluorescent intensity versus the change in anion concentration, with respect to various types of anions, by using the fluorescent sensor of the present invention.

As expressed by the formula (1), the phosphate anion-selective fluorescent compound for use in the fluorescent sensor of the present invention is a new type of fluorescent probe for anion detection, which is composed of a zinc-binuclear complex of 2,2'-dipicolylamine (hereinafter abbreviated as Dpa) and zinc. Preferred examples of the fluorescent functional group or atomic group having an aromatic ring or heterocyclic ring, represented by FL in the formula (1), are those expressed by the following formulae (a), (b), (c) or (d) in (2).

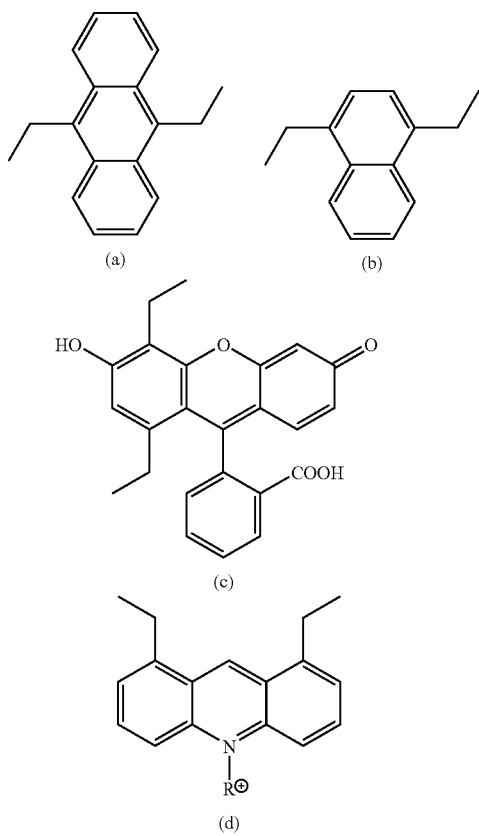

(2)

(a)  (b)

(c)

(d)

In the formula (d), R represents hydrogen atom, an alkyl group having 1 to 4 carbon atoms or benzyl group. Preferred examples of the functional group or atomic group which will be liberated in an aqueous solution to form anion, represented by X in the formula (1), include $NO_3$, a halogen atom (particularly chlorine or iodine), and $ClO_4$ (perchlorate ion).

Thus, as an example of a particularly preferred phosphate anion-selective fluorescent compound composing the fluorescent sensor of the present invention for phosphate ion and phosphorylated peptides, there may be given the compound expressed by the following formula (3) (hereinafter the compound of the formula (3) is sometimes abbreviated as Zn(Dpa)-9,10-Anth complex.)

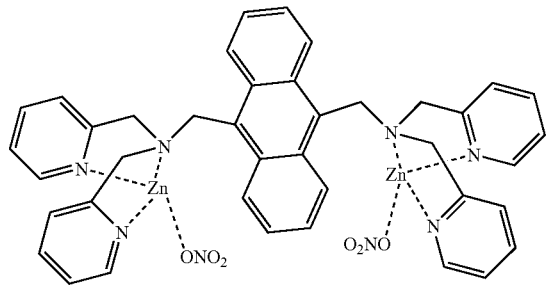

(3)

A metal complex of the formula (1), as typified by the compound of the formula (3), is a phosphate anion-selective fluorescent compound which exhibits a marked change in fluorescence in the presence of phosphate anions. This is presumably caused by the fact that a compound expressed by the formula (1) will selectively capture a phosphate anion in an aqueous medium through the replacement of X with the phosphate anion, resulting in the appearance of the change in fluorescence.

Thus, fluorescent compounds expressed by the formula (1) functions as highly selective sensors for the qualitative and quantitative analysis of phosphate anion which exhibits a clear change in fluorescence in the presence of phosphate anions whose concentration is as low as the uM order of magnitude (cf. Example 2 below).

A fluorescent compound expressed by the formula (1) exhibits a fluorescence response not only to isolated phosphate ion but also to certain phosphorylated peptides. Specifically, the fluorescent compound of the present invention has a high affinity for a peptide composed of an amino acid sequence containing a hydrophobic amino acid (residue) and an anionic amino acid (residue) in addition to a phosphorylated amino acid (residue), exhibiting a change in fluorescence corresponding to the change in the concentration of the peptide. This is probably because the compounds of the present invention, which contain aromatic and/or heterocyclic rings, generally have a cationic charge of four valence in total. Thus, the compound of the present invention composed of a zinc-dipicolylamine binuclear complex as expressed by the formula (1) functions as a sequence-selective sensor for phosphorylated peptides (cf. Example 3 below).

The fluorescent compounds expressed by the formula (1) can be easily synthesized through a scheme of known reactions. FIG. 1 outlines a scheme for synthesizing the fluorescent compound of the formula (1) for use in the present invention. As can be seen from FIG. 1, a brominated precursor compound (A) having a fluorescent functional or atomic group is rendered to react with 2,2'-dipicolylamine (B) in the presence of potassium carbonate to produce a compound (C) in which two Dpa's are combined with each other via the fluorescent functional or atomic group. A desired metal complex (1), a fluorescent compound, can be obtained simply by mixing the compound (C) with an X salt of zinc (ZnX). More specifically, the synthesized receptor molecule is just admixed with a zinc salt (e.g. zinc nitrate) in an aqueous solution having an adjusted pH value with an appropriate buffer solution (e.g. borate buffer) to produce a desired complex, because zinc is active in the ligand substitution and the reaction attains equilibrium very rapidly.

EXAMPLES

While the features of the present invention will be explained in a more concrete manner with reference to the following working examples, the examples are not for restricting the invention.

In the chemical formulae shown in the subject specification and drawings, carbon atoms and/or hydrogen atoms are sometimes omitted in accordance with the traditional expression. The broken lines in the chemical formulae indicate coordinate bonds.

Example 1

Synthesis of Fluorescent Compound

As a fluorescent compound of the present invention, Zn(Dpa)-9,10-Anth complex, as expressed by the aforementioned formula (3), was synthesized as follows.

Firstly, a compound in which two Dpa's are combined with one another via a demethylanthlyl group (a compound C in FIG. 1) was synthesized in the following manner: Into a 50 ml two-necked flask were charged potassium iodide 0.12 g, potassium carbonate 1.05 g, 9,10-bis(chloromethyl) anthracene (A) 0.50 g. Following deaeration with nitrogen, the mixture was dissolved in 10 ml dimethylformamide. On adding 0.6 ml dipicolylamine (B), the resultant was kept at 35° C. for six hours and then at 45° C. overnight while being stirred. The insolubles were subjected to filtration and the filtrate was distilled off in vacuo. The resultant residue was dissolved in chloroform, followed by washing with 0.01N sodium hydroxide aqueous solution. The organic phase was concentrated and purified by chromatography with silica gel resulting in a yellowish solid. The identification was carried out by MNR and elemental analysis.

Calculated: C, 79.97; H, 6.04; N, 13.99. Found: C, 79.84; H, 6.04; N, 13.99.

Then, the compound 45.06 mg thus obtained was dissolved in methanol and added with 3 ml of 50 mM zinc nitrate aqueous solution, and the resultant was stirred. After the methanol was distilled off in vacuo, the resultant was subjected to lyophilization, yielding the compound of the formula (3) as a yellowish solid. The identification was carried out by mass spectrometry and elemental analysis. MS (Calculated molecular weight: 852.75. Found: 852.94). Elemental Analysis (Calculated: C, 47.31; H, 3.97; N, 13.79. Found: C, 47.20; H, 3.93; N, 13.74).

Example 2

Experiment on Anion-Selectivity

Using Zn(Dpa)-9,10-Anth complex prepared in Example 1 as a fluorescent compound of the present invention, measurements were conducted on fluorescence change with changing concentration of anions. The types of anion measured were phosphate ion, acetate ion, nitrate ion, sulfate ion, azide ion, fluoride ion, chloride ion and bromide ion, all of which were dissolved as sodium salt in an aqueous solution. The experimental conditions were as follows.

Concentration of Zn(Dpa)-9,10-Anth complex: 10 µM
Concentrations of the anions: 0, 10, 20, 30, 100, 500, 1000, 2000 µM (0~200 eq.)
Aqueous solution: pH 7.2, 10 mM, HEPES buffer
Measurement temperature: 20° C.
Measurement cell: 1 cm cell
Excitation wavelength λex: 380 nm (ex/em=2.5/2.5 nm)

The results of the measurements are given in FIG. 1. As shown by the figure, there were observed no substantial changes in the fluorescence intensity with anions other than phosphate anion. Thus, it was concluded that the Zn(Dpa)-9,10-Anth complex according to the present invention exhibits a high-selectivity for phosphate anion and functions as a highly sensitive sensor for the analysis of phosphate anion.

Example 3

Experiment on Sequence-Selectivity to Peptides

Using Zn(Dpa)-9,10-Anth complex of the aforementioned formula (3), experiments were conducted on fluorescence change when the complex reacts with peptides having varying sequences, so as to evaluate the selectivity thereto. For comparison, a similar experiment was carried out using a mononuclear complex having only a single Zn(Dpa) as expressed by the formula (4) below (The compound of the formula (4) is hereinafter abbreviated as Zn(Dpa)-9,10-Anth complex).

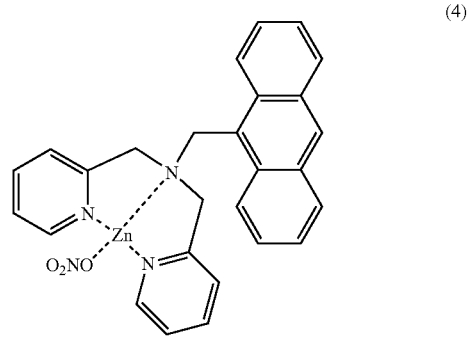

(4)

Synthesis of Peptides

Figures 3, 4:
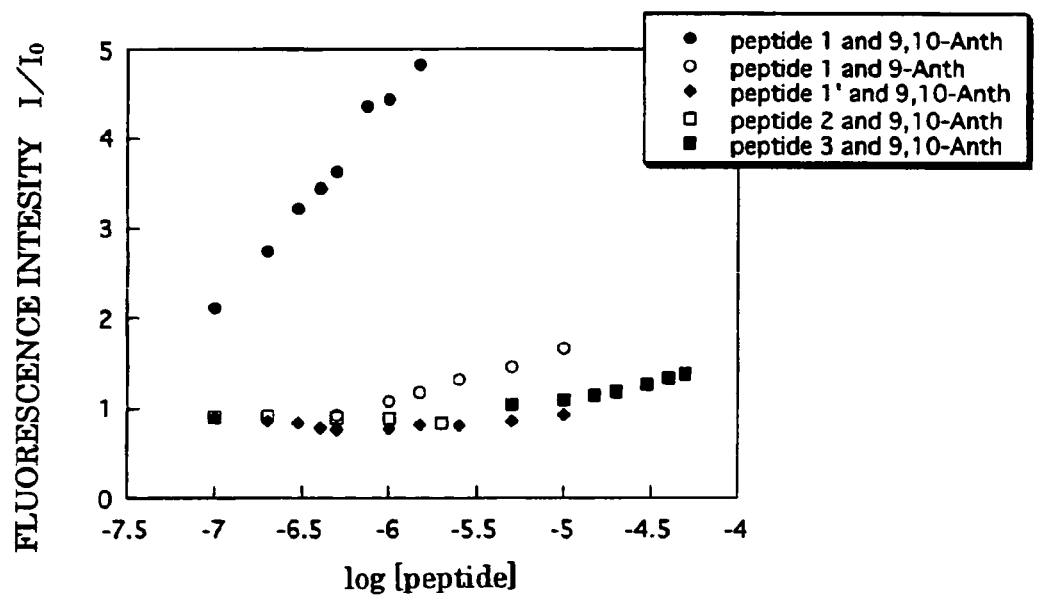
FIG. 3 shows the amino acid sequence of the peptide employed in the study of the sequence selectivity of the fluorescent sensor of the present invention.
FIG. 4 illustrates an example of the measurements of the change in fluorescent intensity versus the change in peptide concentration, with respect to peptides having various amino acid sequences, by using the fluorescent sensor of the present invention.

The experiment was carried out using peptides having amino acid sequences as shown in FIG. 3. The N-terminus of each peptide is protected through acethylation while the C-terminus thereof is of an amide structure. The amino acid sequences of peptides 1, 1', 2 and 3 are listed, in the later-mentioned Sequence Listing, as the Sequence Nos. 1, 2, 3 and 4, respectively. Peptides 1, 2 and 3 each constructs a consensus sequence for phosphorylation by a kinase as shown in the parentheses in FIG. 3. Each sequence was employed for the reasons of the following characteristic features.

Peptide 1: A peptide having a phosphorylated amino acid (Tyr at the position 5) as well as a hydrophobic amino acid and a negatively charged amino acid.

Peptide 1': A peptide as a control of peptide 1, not having the phosphorylated amino acid.

Peptide 2: A peptide having a phosphorylated amino acid (Ser at the position 5) as well as a hydrophobic amino acid while having a number of positively charged amino acids.

Peptide 3: A peptide having a phosphorylated amino acid (Tyr at the position 4) as well as a hydrophobic amino acid while having an equal number of positively and negatively charged amino acids so that the overall electric charge is neutralized.

Each peptide was automatically synthesized by a peptide synthesizer. Fmoc amino acid (0.4 mmol) was used in an amount of four times that of amide resin (introduction: 0.64, scale: 0.1 mmol). HBTU was used as a condensation agent, which deprotected the N-terminal amino acid. Following the automatic condensation, the resultant resin was transferred to a disposable column, and well washed with methylene chloride. Then, there were added methylene chloride 5 ml and acetic acid anhydride 0.8 ml, followed by stirring. The reaction was allowed to proceed until there were absolutely no free amino groups, while tracing the process of the reaction by means of the kayser test. On completion of the reaction, the product was well washed with methylene chloride and then subjected to vacuum drying in a desiccator.

The resin thus obtained 50 ml was placed in a round-bottom flask and added with separating-deprotecting agents, m-cresol, thioanisole and TFA, in amounts of 0.06 ml, 0.36 ml and 2.58 ml, respectively, for 300 mg of the resin. The resultant was stirred for one hour at room temperature. The resin was then subjected to filtration and the filtrate was distilled off in vacuo. After adding TBME, a crude peptide was obtained as precipitate by filtration, which was then subjected to vacuum drying. The crude peptide thus obtained was dissolved in NMP and the target peptide was isolated by HPLC. The identification was carried out by MALDI-TOF-MS.

Evaluation of Peptide-Selectivity

The peptide-selectivity in an aqueous solution was evaluated by fluorescence measurement. The conditions for the measurement were as follows.

Concentrations of peptides: 0-10 eq. The concentrations of peptide 3 were 0 to 5 eq.
Aqueous solution: pH 7.2, 50 mM, HEPES buffer
Measurement cell: 1 cm cell
Excitation wavelength $\lambda_{ex}$: 380 nm (slit width ex/em=5/10 nm)

The results of the measurements are shown in FIG. 4. As can be seen from FIG. 4, only Zn (Dpa)-9,10-Anth complex has a high affinity only for a peptide having both a phosphorylated amino acid and a hydrophobic amino acid, while having a negatively charged amino acid (peptide 1), and exhibits a marked change in the fluorescence intensity with changing concentration of the peptide. Thus, it was concluded that Zn(Dpa)-9,10-Anth complex according to the present invention functions as a sequence-selective sensor for phosphorylated peptides.

Industrial Applicability

It is evident from the foregoing explanation that the zinc-dipicolylamine binuclear complex according to the present invention functions as a highly sensitive fluorescent sensor for phosphate ion and is also useful as a highly sensitive sequence-selective sensor for phosphorylated peptide, in an aqueous solution corresponding to an in vivo environment. The present invention thus provides a promising research tool for studying in vivo reaction mechanisms, thereby contributing to the development of novel medicines, reagents, functional elements and the like.

The invention claimed is:

1. A method comprising:

in an aqueous solution, providing a fluorescent sensor for phosphate ion and phosphorylated peptide, which sensor comprises a phosphate anion-selective fluorescent compound expressed by the following general formula (1):

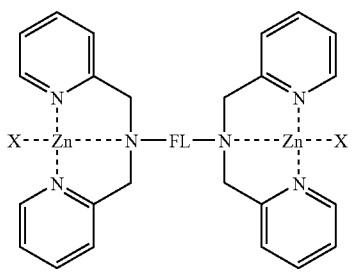

(1)

wherein FL represents a fluorescent functional group or atomic group having an aromatic ring or heterocyclic ring, and X represents a functional group or atomic group which is liberated in an aqueous solution to form an anion; and sensing at least one of phosphate ion and phosphorylated peptide in the aqueous solution as a change in fluorescent intensity, wherein said phosphorylated peptide is composed of an amino acid sequence containing a hydrophobic amino acid and an anionic amino acid in addition to a phosphorylated amino acid.

2. The method of claim 1, wherein FL is selected from one of (a), (b), (c) and (d) in the following (2):

(2)

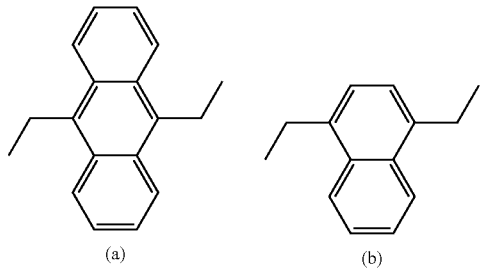

(a)  (b)

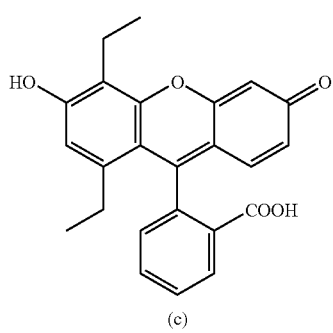

(c)

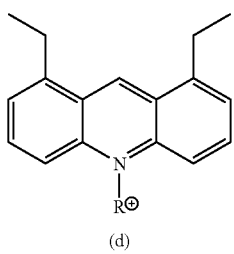

(d)

wherein R represents hydrogen atom, an alkyl group having 1 to 4 carbon atoms or benzyl group in the formula (d).

3. The method of claim 1, wherein X is $NO_3$, a halogen atom or $ClO_4$.

4. The method of claim 2, wherein X is $NO_3$, a halogen atom or $ClO_4$.

5. The method of claim 1, wherein said phosphorylated peptide exhibits a change in fluorescence corresponding to a change in concentration of the phosphorylated peptide and said method includes determining a concentration of said phosphorylated peptide based on said change in fluorescence.

6. An aqueous solution comprising:

a fluorescent sensor which comprises a phosphate anion-selective fluorescent compound expressed by the following general formula (1):

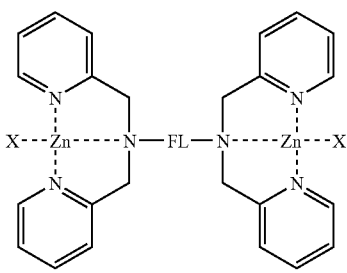

(1)

wherein FL represents a fluorescent functional group or atomic group having an aromatic ring or heterocyclic ring, and X represents a functional group or atomic group which is liberated in the aqueous solution to form an anion; and a phosphate ion or phosphorylated peptide in sufficient amount to produce a fluorescence change, wherein said phosphorylated peptide is composed of an amino acid sequence containing a hydrophobic amino acid and an anionic amino acid in addition to a phosphorylated amino acid.

7. The solution of claim 6, wherein FL is selected from one of (a), (b), (c) and (d) in the following (2):

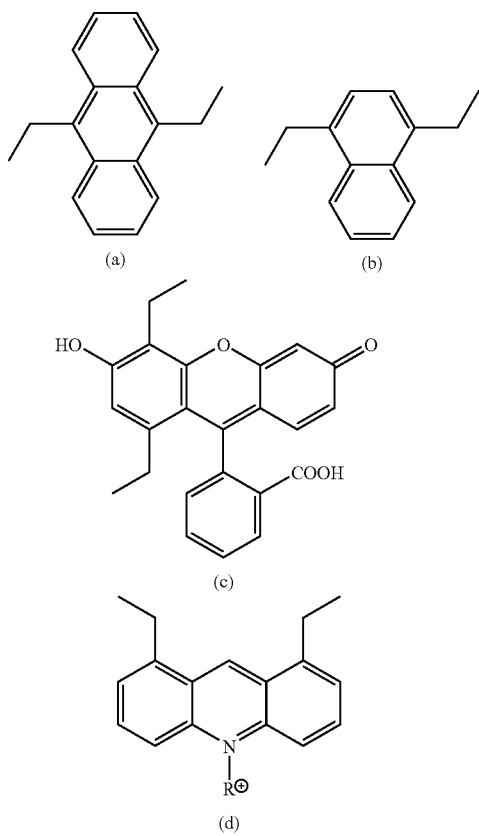

(a) (b) (c) (d)

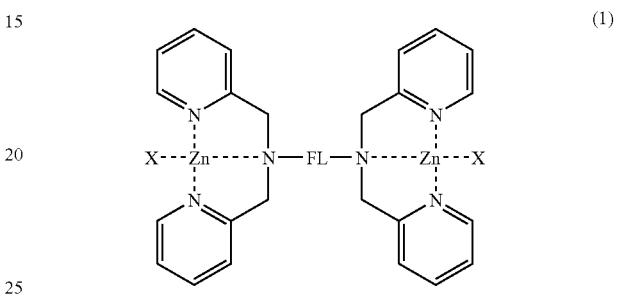

(1)

wherein FL represents a fluorescent functional group or atomic group having an aromatic ring or heterocyclic ring, and X represents a functional group or atomic group which is liberated in an aqueous solution to form an anion; and sensing an exhibited change in fluorescent intensity of the solution corresponding to a change in concentration of the phosphorylated peptide in the aqueous solution.

wherein R represents hydrogen atom, an alkyl group having 1 to 4 carbon atoms or benzyl group in the formula (d).

8. The solution of claim 6, wherein X is $NO_3$, a halogen atom or $ClO_4$.

9. The solution of claim 7, wherein X is $NO_3$, a halogen atom or $ClO_4$.

10. A method comprising:

in an aqueous solution containing a phosphorylated peptide, providing a fluorescent sensor which comprises a compound expressed by the following general formula (1):

* * * * *